United States Patent [19]

Bardin et al.

[11] Patent Number: 5,342,834
[45] Date of Patent: Aug. 30, 1994

[54] METHOD FOR ANDROGEN SUPPLEMENTATION

[75] Inventors: C. Wayne Bardin, New York, N.Y.; Carl Monder, Teaneck, N.J.

[73] Assignee: The Population Council, Inc., New York, N.Y.

[21] Appl. No.: 962,043

[22] Filed: Oct. 15, 1992

Related U.S. Application Data

[63] Continuation of Ser. No. 335,039, Apr. 7, 1989, abandoned.

[51] Int. Cl.$^5$ .............................................. A61K 31/56
[52] U.S. Cl. ..................................... 514/178; 514/179
[58] Field of Search ................................ 514/178, 179

[56] References Cited

U.S. PATENT DOCUMENTS

| | | | |
|---|---|---|---|
| 3,341,557 | 9/1967 | Babcock et al. | 260/397.3 |
| 4,412,993 | 11/1983 | Sokolowski | 514/177 |
| 4,701,450 | 10/1987 | Kelder et al. | 514/177 |

OTHER PUBLICATIONS

Endocrinology, vol. 119, No. 3 pp. 959–966; Blohm et al., 1986.
Androgens and Anabolic Agents (1969) pp. 1, 2, 19, 59–62, 77–78; Vida.
"In vitro Metabolism of 7-αalpha –methyl–19–Nortestosterone by Rat Liver, Prostate, and Epididymis", A. K. Agarwal and C. Monder, Endocrinology, vol. 123, No. 5, 1988, pp. 2187–2193.

*Primary Examiner*—Marianne M. Cintins
*Assistant Examiner*—Kimberly R. Jordan
*Attorney, Agent, or Firm*—Brumbaugh, Graves, Donohue & Raymond

[57] ABSTRACT

A particular group of androgens is not metabolized to their 5α-reduced form in the prostate and other tissues. Thus, administration of these compounds—testosterone derivatives with a non-hydrogen substituent in the 6α or 7α position—allows one to provide androgen supplementation therapy without stimulating abnormal prostate growth. A preferred compound for use in the invention is 7α-methyl-19-nortestosterone.

6 Claims, 1 Drawing Sheet

METHOD FOR ANDROGEN SUPPLEMENTATION

This application is a continuation of application Ser. No. 07/335,039, filed on Apr. 7, 1989, now abandoned.

BACKGROUND OF THE INVENTION

This application relates to a method of providing androgen therapy to human male patients. More particularly, the application relates to a method of providing androgen supplementation without inducing an abnormal weight gain in the prostate.

In men, the prostate progressively enlarges throughout life. In some individuals obstruction of the urethra occurs so that the bladder will not empty efficiently. Surgery is often required to remove the portion of the prostate that obstructs the outflow of urine. Although not all of the factors which promote the continued growth of the prostate are understood, it is clear that prostate growth does not occur in the absence of testosterone, the major androgen secreted by the testes. Therefore, in men who need androgen replacement therapy, an approach which would minimize androgen delivery to the prostate cell could lessen the need for prostate surgery.

Androgen therapy in the human male has been used to treat sexual impotence and infertility, to induce sexual maturation at time of expected puberty and to maintain secondary sexual characteristics. Androgen therapy can also be used as a component of a male contraceptive. With the exception of contraception, these diverse conditions are in general manifestations of defective testicular function either primary or secondary, which results in insufficient testosterone production. As such, they are effectively treated by administration of an androgenic hormone such as testosterone.

Testosterone and its esters, e.g. testosterone enanthate and caproate, that are commonly used to treat androgen deficiency are not particularly potent androgens. As a consequence, 200 mg per month or more must be administered to achieve the desired level of activity. Since such a dose increases the risk of adverse side effects, a large number of testosterone analogs have been developed and tested for androgenic activity (see, e.g. Liao et al. J. Biol. Chem. 248, 6154–6162 (1973)), and many have been found to possess superior activity. These "super androgens" can therefore be used at much lower dosage levels than the natural androgen testosterone.

Merely being able to reduce the dosage level does not overcome all of the potential problems associated with testosterone therapy. This is because testosterone does not interact with all body tissues equally. Testosterone is converted in some tissues, notably the prostate, seminal vesicles, epididymides, and skin to 5α-dihydrotestosterone (DHT) which serves as the intracellular androgen in these organs. In contrast, in most other tissues of the body such as the brain, pituitary, muscle, kidney, etc. testosterone per se is the active intercellular androgen and it is not converted to DHT when testosterone is administered at a dose that will maintain libido (action on the brain) and anabolic activity (action on muscles).

Since DHT is a much more potent androgen than testosterone the effects of testosterone are amplified in tissues where DHT is produced. Thus, the prostate is provided with an unnecessarily high dose of androgen in the form of DHT when maintenance levels of testosterone are present. The resulting stimulation of prostate can cause unnecessary growth leading eventually to a potential need for prostate surgery. This amplification of an administered steroid, by way of its conversion to a more potent product, has also been observed for some of the more potent androgens. Thus, the administration of a lower dose of one of the potent androgens does not necessarily solve this problem associated with androgen therapy.

SUMMARY OF THE INVENTION

It has now been found, however, that a particular group of androgens is not metabolized to their 5α-reduced form in the prostate and other tissues. Thus, administration of these compounds—testosterone derivatives with a non-hydrogen substituent in the 6α or 7α position—allows one to provide androgen supplementation therapy without stimulating abnormal prostate growth. A preferred compound for in the invention is 7α-methyl-19-nortestosterone.

DETAILED DESCRIPTION OF THE INVENTION

Figure 1:
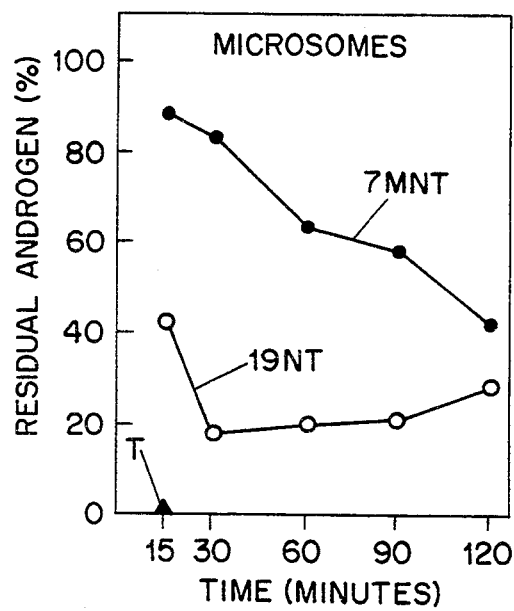
FIG. 1 shows the change in testosterone, 19-nortestosterone and 7MNT levels during incubation with microsomal fractions of rat liver.

Compounds useful in the method of the invention are testosterone derivatives having a non-hydrogen substituent in the 6α or 7α position. As used in the application, the term testosterone derivatives encompasses compounds having the basic four ring structure of testosterone, optionally modified at the 3, 5, 9, 11, 17 or 19 positions. Specific examples of such compounds include:

7-α-methyl testosterone
7-α-methyl-19-nortestosterone
7-α-methyl-11β-hydroxytestosterone
7-α,17-dimethyltestosterone
7-α,17-dimethyl-11β-hydroxytestosterone
7-α,17-dimethyl-19-nortestosterone
7-α,17-dimethyl-11β-hydroxy-19-nortestosterone
6-α-methyl testosterone
6-α-methyl-19-nortestosterone
6-α-methyl-11β-hydroxytestosterone
6-α,17-dimethyltestosterone
6-α,17-dimethyl-11β-hydroxytestosterone
6-α,17-dimethyl-19-nortestosterone
6-α,17-dimethyl-11β-hydroxy-19-nortestosterone Preferred among these compounds by virtue of its high potency and its lack of significant non-androgenic activity (e.g. progestational activity) is 7α-methyl-19-nortestosterone (7MNT).

The 7α-methyl testosterone compounds for use in the invention can be prepared as described in U.S. Pat. No. 3,341,557 which is incorporated herein by reference. For example, 7α-methyl-19-nortestosterone can be prepared via the acetate intermediate.

To prepare 7α-methyl-19-nortestosterone acetate, to 30 ml. of tetrahydrofuran (prepared by percolating commercial grade tetrahydrofuran through a column of neutral alumina and discarding the first 15 ml of percolate) cooled in an ice-bath is added, with stirring under an atmosphere of nitrogen, 25 ml. of a 3M solution of methylmagnesium bromide in ether followed of 0.4 g of cuprous bromide. To the stirred mixture so obtained is added a slurry of a small amount of cuprous bromide in a solution of 3 g of 6-dehydro-19-nortestosterone 17-acetate in 50 ml. of tetrahydrofuran (previously treated as described above). The resulting mixture is stirred with cooling for a further ten minutes and is then poured into a mixture of ice-diluted hydrochloric acid saturated with sodium chloride-ether which is purged with nitrogen. The ether phase is separated and washed successively with brine, diluted sodium hydroxide-brine and finally with brine. The ether extracts are combined and dried over anhydrous magnesium sulfate. The dried solution is filtered and the fitrate is evaporated to dryness. The residue is dissolved in 5 ml. of pyridine and 5 ml. of acetic anhydride. After standing at room temperature for 18 hrs., ice and water are added and the product is extracted with ether. The extract is washed with dilute acid, dilute sodium hydroxide and water, dried and the solvent removed. The residue is dissolved in methylene chloride and chromatographed on a column of magnesium silicate (Florisil). The column is eluted with Skellysolve B hexanes containing increasing proportions of acetone and those fractions which are found by infrared analysis to contain the desired 7α-methyl-19-nortestosterone 17-acetate are combined and evaporated to dryness. The oily residue is dissolved in acetone and chromatographed on a 30 g 2:1 Celite: Darco column packed wet with acetone. The column is eluted with acetone and the first 750 ml of eluate was evaporated to dryness. The residue is recrystallized from aqueous methanol.

To prepare 7α-methyl-19-nortestosterone, a solution of 3 g of 7α-methyl-19-nortestosterone-17-acetate in 40 ml of a 5 percent solution of potassium carbonate in 80 percent aqueous methanol is heated under reflux in an atmosphere of nitrogen for 2 hours. The reaction mixture is extracted with ether and the ethereal extract is washed with water and dried over anhydrous magnesium sulfate. The dried ether solution is filtered and the filtrate is evaporated to dryness. The residue is triturated with ether and the solid which separates is isolated by filtration. There is thus obtained 7α-methyl-19-nortestosterone in the form of a crystalline solid having a melting point of 140° to 145.5° C.

An isomeric mixture of 7α-methyl and 7β-methyl Δ4-3-ketones also may be prepared by cuprous chloride catalyzed addition of methyl Grignard reagent to a 3-oxo-4,6-diene. (e.g. J. A. Campbell and J. C. Babcock 7α-methyl-testosterones, A New Class of Potent Anabolic Agents in Proc. First. Intern Congr. Hormonal Steroids, L. Martini and A. Pecile (editors) Academic Press, NY, Vol. 2, pp 59–67)

The 6α-testosterone derivatives of the invention can be prepared by treating a 5α-,6α-epoxy intermediate with methylmagnesium bromide in a high boiling solvent (e.g. benzene). A 6β-methyl-5α-hydroxy product is generated as a result of trans-diaxial opening. The desired 6α-methyl-3-oxo-4-ene is obtained by oxidation and dehydration of the intermediate. Examples of synthesis in the androstane series are found in H. J. Ringold, E. Batres and G. Rosenkranz, J. Org. Chem., 22 99 (1957); M. Ackroyd, W. J. Adams, B. Ellis, V. Petrow and I. A. Stuart-Webb, J. Chem. Soc. 1957, 4099).

The amount of testosterone derivative which is appropriately administered will depend on two factors—the potency of the compound and the route of administration. In general, potency can be determined relative to testosterone or some other standard androgen and the dosage calculated with reference to the accepted therapeutic amount of the known compound. For example, the usual dosage of testosterone enanthate (one of the most commonly used replacements for testosterone in humans) is about 200 mg/month intramuscularly or about 7 mg/day. Since 7MNT is 15 to 20 times more potent an androgen than testosterone, the appropriate dose of 7MNT will be about 10 to 20 mg/month or 0.3 to 0.6 mg/day.

EXAMPLE

The metabolism of 7MNT, testosterone (T) and 19-nortestosterone (19NT) in rat liver, ventral prostate and epididymis was tested.

To prepare rat liver microsomes and cytosol, thawed livers were homogenized in 4 vol. of TED buffer (10mM Tricine, 1.5 mM EDTA, 1 mM dithiothreitol, pH 7.4) using a glass homogenizer and a loosefitting Teflon piston for nine strokes with intermittent cooling. This and all subsequent steps were performed at 4° C. The homogenate was spun at 13000×g for 30 min in a Sorvall refrigerated centrifuge. The supernatant fraction was recentrifuged at 13000×g for another 30 min. The resulting supernatant fraction (13K supernatant) was centrifuged at 105,000×g using a Beckman Ultracentrifuge (Model L) for 60 min. The 105K supernatant (cytosol) was saved. The microsomal pellet was resuspended in TED buffer, and spun down again at 105,000×g. The resulting pellet is known as the 105K pellet of the microsome fraction (or "microsome").

Incubation mixtures consisted of 52 nmol of unlabeled steroid (T, 7MNT or 19NT), approximately 40,000 CPM of the corresponding tritiated steroid and 5 umol of NADPH in 0.2 ml TED buffer (pH 7.4). This was incubated for 10 min at 37° C. in a constant temperature water bath. Reaction was initiated by the addition of 0.8 ml of either 13K supernatant, microsomes or cytosol, containing 7.05, 0.62 or 5.64 mg/ml of protein, respectively. Incubations were quenched with 2 ml of ethyl acetate, vortexed briefly, and frozen in a dry ice-alcohol bath. The ethyl acetate was separated from the frozen aqueous phase. Extraction was performed again in the same way. The combined organic phase was evaporated and the remaining steroids were analyzed.

In preparation for the isolation and identification of unlabelled steroid metabolites in the microsome preparations, 360 μg of 7MNT were dispensed into 24 tubes in parallel with identical tubes containing $^3$H-labeled 7MNT to be used as marker steroid. The mixtures were incubated for 60 min at 37° C., extracted twice with 2 ml of ethyl acetate, taken to dryness, redissolved in a mixture of dichloromethane/methanol (1:1, v/v) and quantitatively applied to silica gel coated TLC plates along with synthetically prepared suspected metabolites of radioactive 7MNT in a parallel lane. The plates were developed with chloroform/methanol (95:5, v/v). Spots corresponding to the radioactive marked spots were eluted with ethyl acetate and taken to dryness.

The procedure used for the cytosol preparations was the same as that for microsomes, except that incubations were carried out for 90 min.

For isolation of radioactive metabolites, the procedure was the same as for unlabeled metabolites, except that each tube contained 50,000 CPM of $^3$H-labeled 7MNT.

Various derivatives of the radioactive metabolites were also prepared. Acetylated metabolites were made by first dissolving the radioactive steroid metabolites (10,000 CPM) in 50 μl of anhydrous pyridine. Reaction was initiated with 50 μl of acetic anhydride. After 12 to 18 h at room temperature, solvent was evaporated under nitrogen. The ester derivative redissolved in 20 μl of methanol was applied to TLC plates along with starting metabolite. The plates were developed using dichloromethane/ethyl acetate (7:3) as the mobile phase and the radioactivity was scanned on the Bioscan imaging scanner.

Recovered radioactive metabolites were oxidized with Jones reagent (22). Reagent was prepared by dissolving 4.04 g of potassium chromate in 21.5 ml of distilled water followed by dropwise addition of 3.5 ml of concentrated sulfuric acid; immediately before initiating the reaction, 0.1 ml of reagent was diluted with 10 ml of acetone. The diluted reagent (50 μl) was added to the steroid. The mixture was left at room temperature for 20 min. The reaction was quenched by adding 1.0 ml of ice-cold water. The diluted mixture was poured onto a 3 ml Extrelut column (to extract the steroids). The reaction tubes were washed twice with 1 ml of water each time and the washings were added to the column. Steroids were eluted with 12 ml of ethyl acetate. The solvent was then evaporated under nitrogen. The residual steroids were dissolved in methanol, applied on TLC plates, developed using dichloromethane/ethyl acetate (7:3) and scanned for radioactivity.

To prepare diazomethane derivatives, the radioactive metabolites obtained from cytosol and microsomes were oxidized with Jones reagent as described above. The oxidized product was dissolved in 0.5 ml of MeOH. To this was added at 10 min intervals two doses of 0.5 ml of freshly prepared diazomethane. The mixture was vortexed briefly and left at room temperature for 30 min. Solvents were evaporated under nitrogen. The derivative was dissolved in methanol and applied on TLC plates. Chromatograms were developed using chloroform/methanol (95:5) as mobile phase, and scanned for radioactivity.

A DuPont model 21-492 double focusing magnetic sector mass spectrometer coupled to a VG Datasystem 2040 was also used to identify recovered metabolites. The source temperatures were in the range of 120°–150° C. Isobutane was used as the reactant for chemical ionization.

TLC plates were sprayed with a solution of 1.5% vanillin in 1% ethanolic (abs.) sulfuric acid, dried, then exposed for 5–10 mins. at 120°–140° C. The steroids produced different colors depending on the presence of various functional groups Monder et al., "Application of Polyethyleneimine Cellulose for the class Separation of Steroidal Carboylic Acids from Neutral Steroids and Pigments in Urine", Anal. Biochem., 139:237 (1984).

To study metabolism in rat prostate, ventral prostates (1 g) were collected in ice-cold saline. All subsequent operations were carried out at 0°–4° C. The tissues were washed three times with homogenizing buffer (50 mM tris, 1.5 mM EDTA, 1 mM dithiothreitol and 10% glycerol, pH 7.5) and then homogenized in 4 vol. of the same buffer using an Ultra-turrax at a setting of 6. The prostates were given three 10 seconds bursts with intermittent cooling. The resulting homogenate was passed through four layers of cheesecloth and the filtrate was collected.

Incubation mixtures consisted of 50 nmol of unlabeled steroid, 40,000 CPM of the corresponding tritiated steroid and 1 μmol of NADPH in 0.2 ml of the buffer. The mixture was equilibrated for 10 min at 37° C. Reaction was started by adding 0.8 ml of homogenate (5.3 mg/ml protein). After 30 min of incubation, the mixture was cochromatographed with authentic steroids selected as possible metabolites.

The metabolism of T, 19NT and 7MNT by rat epididymis was also studied. Collected epididymides were processed as described for prostate. Incubations were performed in Tricine-buffer pH 7.4 as used for liver incubations. Thin layer chromatography of metabolic mixtures and standards was performed as described for prostate preparations.

Figure 2:
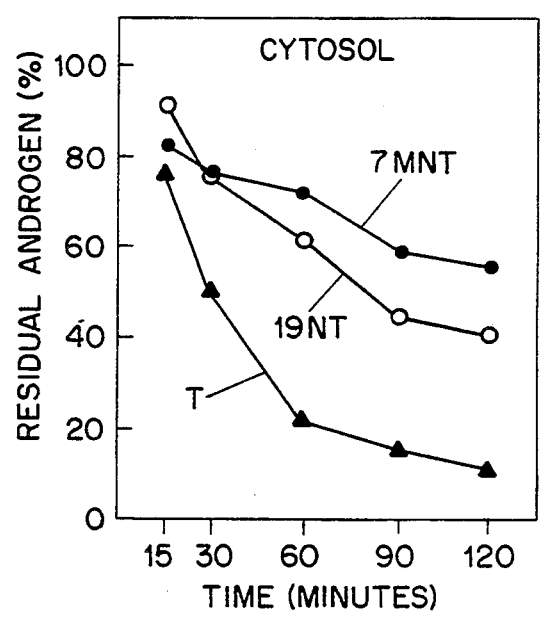
FIG. 2 shows the change in testosterone, 19-nortestosterone and 7MNT levels during incubation with cytosolic fractions of rat liver.

In this series of experiments, the decreases in the levels of testosterone, 19-nortestosterone, and 7MNT were followed over a two-hour period of incubation with microsomal or cytosolic fractions of rat liver. The results of these studies are displayed in FIG. 1 and FIG. 2. Testosterone was completely metabolized by the microsomes before the earliest aliquot was taken at 15 min. The metabolism of 19NT was qualitatively similar to that of T, though slower. Catabolism of 19NT was maximum at 30 min, with no further change beyond that, leaving a persistent unmetabolized residue of about 20 percent of the added steroid. After 30 min of incubation, 85 percent of the 7MNT remained unaltered; forty percent of the 7MNT was recovered after 2h.

In cytosol, about 12 percent of the T remained unmetabolized in 2h. The metabolism of 19NT was still slower; in two hours 40 percent of the steroid was recovered. Half of the starting 7MNT was recovered after 2h incubation.

A detailed study of the metabolism of 7MNT by the rat liver 13K supernatant fraction retaining microsomes and cytosol was undertaken. To follow its fate, about 40,000 CPM of 3H-labeled 7MNT was incubated. A TLC plate showed the metabolites formed after 30 min of incubation at 37° C. in a system enriched with NADPH. The 7MNT was relatively resistant to metabolism under these incubation conditions. Two metabolites, tentatively identified as 7α-methyl-5β-estrane-3, 17β-diol and 7α-methyl-estr-4-ene-3, 17-dione were found. A minor highly polar metabolite was also observed.

Steroid metabolites isolated from incubations of 7MNT with rat liver microsomes were separated on TLC plates with chloroform/methanol (95:5) as mobile phase. After 30 min of incubation, most of the 7MNT was retrieved unaltered. Two significant 7α-methylated metabolites were observed: a less polar one representing the 3,17-dione, and a more polar one in the region of the diols or triols. An additional quantitatively minor polar metabolite was also detected.

Metabolites of 7MNT were isolated after 30 min of incubation with cytosol and analyzed on TLC using chloroform/methanol (95:5) as mobile phase. The steroid generated at least one metabolite that was more polar than the parent compound. The metabolite was probably formed by the action of 5β-reductase and/or soluble 3 and 17-dehydrogenases.

When this same type of analysis was undertaken on the prostate and epididymis samples, it was found that substantially no 5α-dihydro product was formed in either tissue. Table 1 shows that nearly half of the added T was reduced to 5α-DHT when incubated with prostate homogenate. The 19NT was metabolized to the reduced product more slowly than testosterone, resulting in 22% reduced 19NT. Under similar conditions, 7MNT remained unmetabolized.

As with prostate, epididymis did not reduce or otherwise metabolize 7MNT. In contrast T and 19NT were converted to their respective reduced A ring metabolites. 19NT was metabolized more slowly than T.

These results clearly show that 7MNT is not converted to the 5α-dihydro product which is involved in the amplification which occurs in prostate upon administration of testosterone. The failure of 7MNT to undergo 5α reduction is believed to be due to a steric effect of the 7α-methyl group blocking the interaction of the steroid with the reductase. This effect would be expected to occur with 7α-substituted androgens generally and with 6α-substituted androgens as well. Thus, these compounds should prove superior to other androgens of equivalent potency for use in androgen replacement therapy because they do not undergo amplification via metabolism to 5α-reduced product.

One additional application which presents itself is forestalling the effects of testosterone amplification in individuals evidencing early symptoms that are secondary to prostate growth. Since 7MNT has similar potency in tissues which exhibit amplification of testosterone (prostate etc.) and those which do not (brain, kidney, etc.), 7MNT could be used to totally or substantially replace testosterone. If such a patient were treated by administration of a luteinizing hormone releasing hormone (LHRH) analogue or other agent that would suppress testosterone production to a level insufficient to maintain prostate growth, then the libidinous and anabolic effects of testosterone would not be maintained either. These latter effects could be ameliorated by replacement with 7MNT, which would have less of an effect on the prostate than the physiological amount of testosterone. Thus, the progress of conditions symptomatic of testosterone amplification could be slowed.

TABLE 1

METABOLISM OF $^3$H-ANDROGENS BY RAT VENTRAL PROSTATE AND EPIDIDYMIS

| Organ | Androgen (100%) | Conversion of 5α reduced metabolites | |
|---|---|---|---|
| | | 5α-dihydro-steroid (%) | Diols (%) |
| ventral prostate | T | 48 | ND |
| | 19 NT | 22 | ND |
| | 7αMe-19 NT | ND | ND |
| epididymis | T | ND | 86 |
| | 19 NT | ND | 57 |
| | 7αMe-19 NT | ND | ND |

T = testosterone,
19 NT = 19 nor-testosterone,
7αMe-19 NT = 7αmethyl-19-nor-testosterone,
ND = not detectable

We claim:

1. A method for providing androgen hormone supplementation to a human male patient in need of such supplementation without stimulating abnormal growth of the prostate, comprising administering to the patient an effective androgenic amount of a testosterone derivative having a methyl substituent in the 6α or 7α position, wherein the substituent prevents conversion to the 5α reduced form of the testosterone derivative.

2. A method according to claim 1, wherein the testosterone derivative has a greater androgenic potency than testosterone.

3. A method according to claim 2, wherein the testosterone derivative is 7α-methyl-19nortestosterone.

4. A method according to claim 3, wherein the testosterone derivative is administered intramuscularly, subcutaneously or transdermally in an amount of from 5 to 10 μg/kg of body weight.

5. A method of retarding the progress of conditions symptomatic of testosterone amplification in human males exhibiting such symptoms, comprising
   (a) inhibiting testosterone synthesis to below maintenance levels; and
   (b) administering an amount of a testosterone derivative having a methyl substituent in the 6α or 7α position, wherein the substituent prevents conversion to the 5α reduced form of the testosterone derivative and is effective to maintain libidinous and anabolic activity.

6. A method according to claim 5, wherein the testosterone derivative is 7α-methyl-19-nortestosterone.

* * * * *

UNITED STATES PATENT AND TRADEMARK OFFICE
CERTIFICATE OF CORRECTION

PATENT NO. : 5,342,834

DATED : August 30, 1994

INVENTOR(S) : Bardin et al.

It is certified that error appears in the above-indentified patent and that said Letters Patent is hereby corrected as shown below:

Title page, Col. 2, 6th line, "αalpha" should read --alpha--.

Col. 1, under the heading BACKGROUND OF THE INVENTION, insert --This invention was made with the support of the United States Agency for International Development under Cooperative Agreement Number DPE-3050-A-00-8059-00 and from the National Institute of Child Health and Human Development Contract Number HD-29990-02. The Government has certain rights in this invention--.

Col. 2, line 63, "ml." should read --ml--.

Col. 2, line 68, "followed of" should read --followed by--.

Col. 5, line 50, "groups" should read --groups. --.

UNITED STATES PATENT AND TRADEMARK OFFICE
CERTIFICATE OF CORRECTION

PATENT NO. : 5,342,834

DATED : August 30, 1994

INVENTOR(S) : Bardin et al.

It is certified that error appears in the above-indentified patent and that said Letters Patent is hereby corrected as shown below:

<u>Col. 8, line 30</u>, "19nortestosterone" should read --19-nortestosterone--.

Signed and Sealed this

Seventeenth Day of January, 1995

Attest:

BRUCE LEHMAN

Attesting Officer     Commissioner of Patents and Trademarks